(12) United States Patent
Haller et al.

(10) Patent No.: US 7,697,129 B2
(45) Date of Patent: Apr. 13, 2010

(54) SYSTEMS AND METHODS FOR INSPECTING A WAFER WITH INCREASED SENSITIVITY

(75) Inventors: Kurt L. Haller, Pleasanton, CA (US);
David Shortt, Milpitas, CA (US);
Christian Wolters, Campbell, CA (US)

(73) Assignee: KLA-Tencor Technologies Corp., Milpitas, CA (US)

(*) Notice: Subject to any disclaimer, the term of this patent is extended or adjusted under 35 U.S.C. 154(b) by 0 days.

(21) Appl. No.: 12/097,172

(22) PCT Filed: Dec. 14, 2006

(86) PCT No.: PCT/US2006/062097
§ 371 (c)(1),
(2), (4) Date: Jun. 12, 2008

(87) PCT Pub. No.: WO2007/087101
PCT Pub. Date: Aug. 2, 2007

(65) Prior Publication Data
US 2009/0009754 A1    Jan. 8, 2009

(51) Int. Cl.
*G01N 21/00* (2006.01)
(52) U.S. Cl. .................. 356/237.5; 356/237.4
(58) Field of Classification Search ... 356/237.1–241.6, 356/426–431, 600–640
See application file for complete search history.

(56) References Cited

U.S. PATENT DOCUMENTS

| | | | |
|---|---|---|---|
| 3,626,141 A | 12/1971 | Daly | |
| 4,613,207 A | 9/1986 | Fergason | |
| 5,270,781 A | 12/1993 | Singh et al. | |
| 5,531,857 A * | 7/1996 | Engelsberg et al. | 156/345.5 |
| 5,574,276 A | 11/1996 | Ishimaru | |
| 5,669,979 A | 9/1997 | Elliott et al. | |
| 6,005,660 A | 12/1999 | Yoshida et al. | |
| 6,081,325 A | 6/2000 | Leslie et al. | |
| 6,103,537 A | 8/2000 | Ullman et al. | |
| 6,201,601 B1 | 3/2001 | Vaez-Iravani et al. | |

(Continued)

FOREIGN PATENT DOCUMENTS

WO    WO 2006/066135    6/2006

(Continued)

OTHER PUBLICATIONS

Miles et al., "Laser Rayleigh Scattering," Measurement Science & Technology, vol. 12, 2001, pp. R33-R51.

(Continued)

*Primary Examiner*—Gregory J Toatley, Jr.
*Assistant Examiner*—Jarreas C Underwood
(74) *Attorney, Agent, or Firm*—Ann Marie Mewherter

(57) ABSTRACT

Systems and methods for inspecting a wafer with increased sensitivity are provided. One system includes an inspection subsystem configured to direct light to a spot on the wafer and to generate output signals responsive to light scattered from the spot on the wafer. The system also includes a gas flow subsystem configured to replace a gas located proximate to the spot on the wafer with a medium that scatters less of the light than the gas thereby increasing the sensitivity of the system. In addition, the system includes a processor configured to detect defects on the wafer using the output signals.

20 Claims, 4 Drawing Sheets

U.S. PATENT DOCUMENTS

| | | | |
|---|---|---|---|
| 6,271,916 B1 | 8/2001 | Marxer et al. | |
| 6,356,653 B2 | 3/2002 | Brigante et al. | |
| 6,359,212 B1 * | 3/2002 | Hall et al. | 356/239.2 |
| 6,538,730 B2 | 3/2003 | Vaez-Iravani et al. | |
| 6,555,815 B2 | 4/2003 | Feuerbaum et al. | |
| 6,757,048 B2 * | 6/2004 | Arakawa | 355/30 |
| 6,813,026 B2 | 11/2004 | McAninch et al. | |
| 7,061,614 B2 | 6/2006 | Wang et al. | |
| 7,067,819 B2 | 6/2006 | Janik | |
| 7,138,640 B1 * | 11/2006 | Delgado et al. | 250/372 |
| 7,277,171 B1 | 10/2007 | Johs et al. | |
| 7,286,218 B2 | 10/2007 | Tiemeyer et al. | |
| 7,349,079 B2 | 3/2008 | Zhao et al. | |
| 7,359,052 B2 | 4/2008 | Fielden et al. | |
| 7,369,233 B2 | 5/2008 | Nikoonahad et al. | |
| 7,417,722 B2 | 8/2008 | Bills et al. | |
| 2005/0252752 A1 | 11/2005 | Fielden et al. | |
| 2006/0181700 A1 | 8/2006 | Andrews et al. | |
| 2006/0192948 A1 | 8/2006 | Judell et al. | |
| 2006/0192949 A1 | 8/2006 | Bills et al. | |
| 2006/0192950 A1 | 8/2006 | Judell et al. | |
| 2006/0256326 A1 | 11/2006 | Bills et al. | |
| 2007/0024998 A1 | 2/2007 | Bills et al. | |
| 2007/0252977 A1 | 11/2007 | Baran et al. | |

FOREIGN PATENT DOCUMENTS

| | | |
|---|---|---|
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

Stone et al., "Using Helium as a Standard of Refractive Index: Correcting Errors in a Gas Refractometer," Metrologia, vol. 41, 2004, pp. 189-197.

Pendrill, "Macroscopic and Microscopic Polarizabilities of Helium Gas," J. Phys. B: AT. Mol. Opt. Phys., vol. 29, 1996, pp. 3581-3586.

Chan et al., "The Refractive Index of Helium," Proc. Phys. Soc., 1965, vol. 85, pp. 227-230.

Sun et al., "Effects of Gas Medium on Femtosecond Laser Beam Delivery," presented at 21st International Congress on Applications of Lasers & Electro-Optics (ICALEO), Oct. 2002, 10 pages.

Sun et al., "Inert Gas Beam Delivery for Ultrafast Laser Micromachining at Ambient Pressure," Journal of Applied Physics, vol. 89, No. 12, Jun. 2001, pp. 8219-8224.

Sun et al., "Novel Beam Delivery Technique for Ultrafast Laser Processing," Thermal Science & Engineering, vol. 7, No. 6, 1999, pp. 81-85.

International Application No. PCT/US05/45781 filed on Dec. 12, 2005.

* cited by examiner

SYSTEMS AND METHODS FOR INSPECTING A WAFER WITH INCREASED SENSITIVITY

PRIORITY CLAIM

This application is a National Stage application of International Application No. PCT/US06/62097 filed Dec. 14, 2006, which claims priority to U.S. application Ser. No. 11/302,936, filed Dec. 14, 2005, now U.S. Pat. No. 7,372,559, entitled "SYSTEMS AND METHODS FOR INSPECTING A WAFER WITH INCREASED SENSITIVITY."

BACKGROUND OF THE INVENTION

1. Field of the Invention

The present invention generally relates to systems and methods for inspecting a wafer with increased sensitivity. Certain embodiments relate to systems and methods for inspecting a specimen that include replacing a gas proximate to an illuminated spot on the wafer with a medium that scatters less light than the gas thereby increasing the sensitivity of the inspection.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various times during a semiconductor manufacturing process to detect defects on wafers. Inspection has always been an important part of fabricating semiconductor devices such as integrated circuits. However, as the dimensions of semiconductor devices decrease, inspection becomes even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

As the semiconductor industry gears up for the 45 nm node and beyond, integrated circuit (IC) manufacturers are demanding better sensitivity for unpatterned wafer laser surface scanning inspection systems. For example, some IC makers are requiring 25 nm polystyrene latex (PSL) sphere sensitivity on bare polished silicon wafers for three generations beginning at the 45 nm node. This sensitivity is also required at a throughput of 45 wafers per hour. The best performance of most commercially available inspection systems does not meet these sensitivity and throughput performance requirements.

Often, increased sensitivity can be achieved by system configurations that result in reduced throughput. For example, the sensitivity of currently available inspection systems can be increased by reducing the size of the spot on the wafer that is illuminated during inspection. The size of the illuminated spot on the wafer may be reduced relatively simply in many currently used inspection systems (e.g., by altering or adding an optical element to the beam forming optics train). Reducing the spot size effectively decreases the amount of light that is scattered from the surface of the wafer relative to the defect scattering, thereby increasing the defect signal to noise ratio and the sensitivity of the system. However, reducing the spot size also reduces the throughput of the system since scanning a smaller size spot over an entire wafer surface takes longer than scanning a larger size spot over the wafer surface. Therefore, by varying the spot size, it is possible to trade-off throughput for sensitivity.

Other changes can also or alternatively be made to currently available inspection systems to increase the sensitivity of the inspection systems. For example, the collector of some currently available inspection systems may be altered by changing or adding an aperture to the collector. The aperture may be configured to block light that is scattered from the surface of the wafer while allowing light scattered from a defect to pass through the aperture thereby increasing the defect signal to noise ratio of the system and the sensitivity of the system. In another example, the light source of currently available inspection systems may be replaced with a higher power light source. For example, if an inspection system is configured for a laser power of about 350 mW, the laser power of the system can be increased to about 1000 mW. Increasing the power of the light source generally increases the level of light scattered from defects thereby increasing the sensitivity of the system.

Improvements in the surface quality of wafers may also effectively increase the sensitivity of currently used inspection systems. In particular, as the residual surface roughness of wafers such as bare silicon wafers decreases, the amount of light scattered from the wafer surface (i.e., "background scattering") will also decrease. Therefore, the defect signal to noise ratio will increase thereby increasing the sensitivity of the system.

The various improvements in inspection systems and wafer surfaces described above can be used in combination to increase the sensitivity of the systems to various degrees. For example, adding a back aperture as described above and improving the wafer surface may produce a larger increase in sensitivity than adding the back aperture alone. In addition, the degree to which this combination of improvements increases the sensitivity increases with greater improvements in the wafer surface (e.g., from a background scatter of about 30 ppb of the incident laser power to about 15 ppb of the incident laser power). Furthermore, adding a back aperture, improving the wafer surface, and increasing the laser power produces a larger increase in sensitivity than that which can be achieved by adding the back aperture and/or improving the wafer surface.

Obviously, each of the different improvements described above may be implemented at different costs. For instance, improving the sensitivity of the systems by utilizing an aperture and relying on improvements in wafer surfaces is less expensive than increasing the laser power. However, an increase in the laser power may be required to meet the sensitivity requirements described above. Nevertheless, improving sensitivity as described above relies on improvements in wafer surface quality from the typical background scattering observed today (about 80 ppb of the incident laser power) beyond the level of today's best wafer surfaces (background scattering of about 30 ppb of the incident laser power) to ultra-smooth silicon with background scattering of about 15 ppb of the incident laser power.

At such low levels of water-induced background scattering or haze, laser scanning technology has reached the point at which Rayleigh scattering from the air that the laser beam passes through contributes a significant component of the overall background scattering observed. For instance, for some currently available inspection systems, the estimated background scattering due to atmospheric Rayleigh scattering is about 10 ppb of the incident laser power to about 20 ppb of the incident laser power. Obviously, however, the background scattering is dependent on the parameters of the inspection system configuration such as wavelength of illumination, polarization of illumination, optical path length, solid angle of the collector, the depth of field, collection polarization, etc. Therefore, due to atmospheric Rayleigh scattering, a wafer with actual 15 ppb background scattering would look to the detection system like a wafer that has background scattering of about 25 ppb of the incident laser power to about 35 ppb of the incident laser power. Therefore, improvements in sensitivity expected based on improvements in the wafer surface quality cannot be achieved.

Accordingly, it would be advantageous to increase the sensitivity of systems and methods for inspecting a wafer by reducing scattering of light caused by a gas proximate to an illuminated spot on the wafer.

SUMMARY OF THE INVENTION

The following description of various embodiments of systems, gas flow subsystems, and methods is not to be construed in any way as limiting the subject matter of the appended claims.

One embodiment relates to a system configured to inspect a wafer. The system includes an inspection subsystem configured to direct light to a spot on the wafer and to generate output signals responsive to light scattered from the spot on the wafer. The system also includes a gas flow subsystem configured to replace a gas located proximate to the spot on the wafer with a medium that scatters less of the light than the gas thereby increasing the sensitivity of the system. In addition, the system includes a processor configured to detect defects on the wafer using the output signals.

In one embodiment, the medium has a refractive index at visible and ultraviolet (UV) wavelengths that is less than the refractive index of dry air at the visible and UV wavelengths. In some embodiments, the medium consists essentially of elemental helium. In other embodiments, the medium consists essentially of neon.

In another embodiment, the gas flow subsystem is configured to replace the gas with the medium only at a location proximate to the spot on the wafer. In an additional embodiment, the system includes a housing surrounding one or more optical components of the inspection subsystem. In one such embodiment, the gas flow subsystem is configured to purge the housing the medium and to maintain a positive pressure in the housing the medium such that photodecomposition of materials on the one or more optical elements is reduced.

In a further embodiment, the inspection subsystem includes one or more optical components configured to block light scattered along an illumination path of the inspection subsystem such that the output signals are not responsive to the light scattered along the illumination path. In some embodiments, the medium is a vacuum.

In one embodiment, the inspection subsystem is configured as an unpatterned wafer inspection subsystem. In another embodiment, the inspection subsystem is configured as a laser-based inspection subsystem. In an additional embodiment, the light directed to the spot on the wafer includes UV light. In a further embodiment, the inspection subsystem is configured as a scanning-based inspection subsystem. In some embodiments, the increased sensitivity of the system is sufficient for detecting polystyrene latex (PSL) spheres having a diameter of about 25 nm on bare polished silicon wafers. Each of the embodiments of the system described above may be further configured as described herein.

Another embodiment relates to a gas flow subsystem configured to be coupled to an inspection system. The gas flow subsystem is configured to replace a gas located proximate to a spot on a wafer illuminated by the inspection system during inspection with a medium that scatters less of the light than the gas thereby increasing the sensitivity of the inspection system. The gas flow subsystem may be further configured as described herein.

An additional embodiment relates to a method for inspecting a wafer. The method includes inspecting the wafer by directing light to a spot on the wafer and generating output signals responsive to light scattered from the spot on the wafer. The method also includes replacing a gas located proximate to the spot on the wafer during inspecting with a medium that scatters less of the light than the gas thereby increasing the sensitivity of the inspecting. In addition, the method includes detecting defects on the wafer using the output signals.

In one embodiment, the medium has a refractive index at visible and UV wavelengths that is less than the refractive index of dry air at the visible and UV wavelengths. In some embodiments, the medium consists essentially of elemental helium. In other embodiments, the medium consists essentially of neon.

In one embodiment, replacing the gas includes replacing the gas with the medium only at a location proximate to the spot on the wafer. In another embodiment, the method includes purging a housing surrounding one or more optical components used for inspecting with the medium and maintaining a positive pressure in the housing the medium such that photodecomposition of materials on the one or more optical components is reduced.

In a further embodiment, the method includes blocking light scattered along an illumination path along which the light is directed to the wafer such that the output signals are not responsive to the light scattered along the illumination path. In some embodiments, the medium is a vacuum.

In one embodiment, the light directed to the spot on the wafer includes light generated by a laser. In another embodiment, the light directed to the spot on the wafer includes UV light. In some embodiments, inspecting the wafer includes scanning the spot across the wafer. In an additional embodiment, the increased sensitivity of inspecting the wafer is sufficient for detecting PSL spheres having a diameter of about 25 nm on bare polished silicon wafers. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
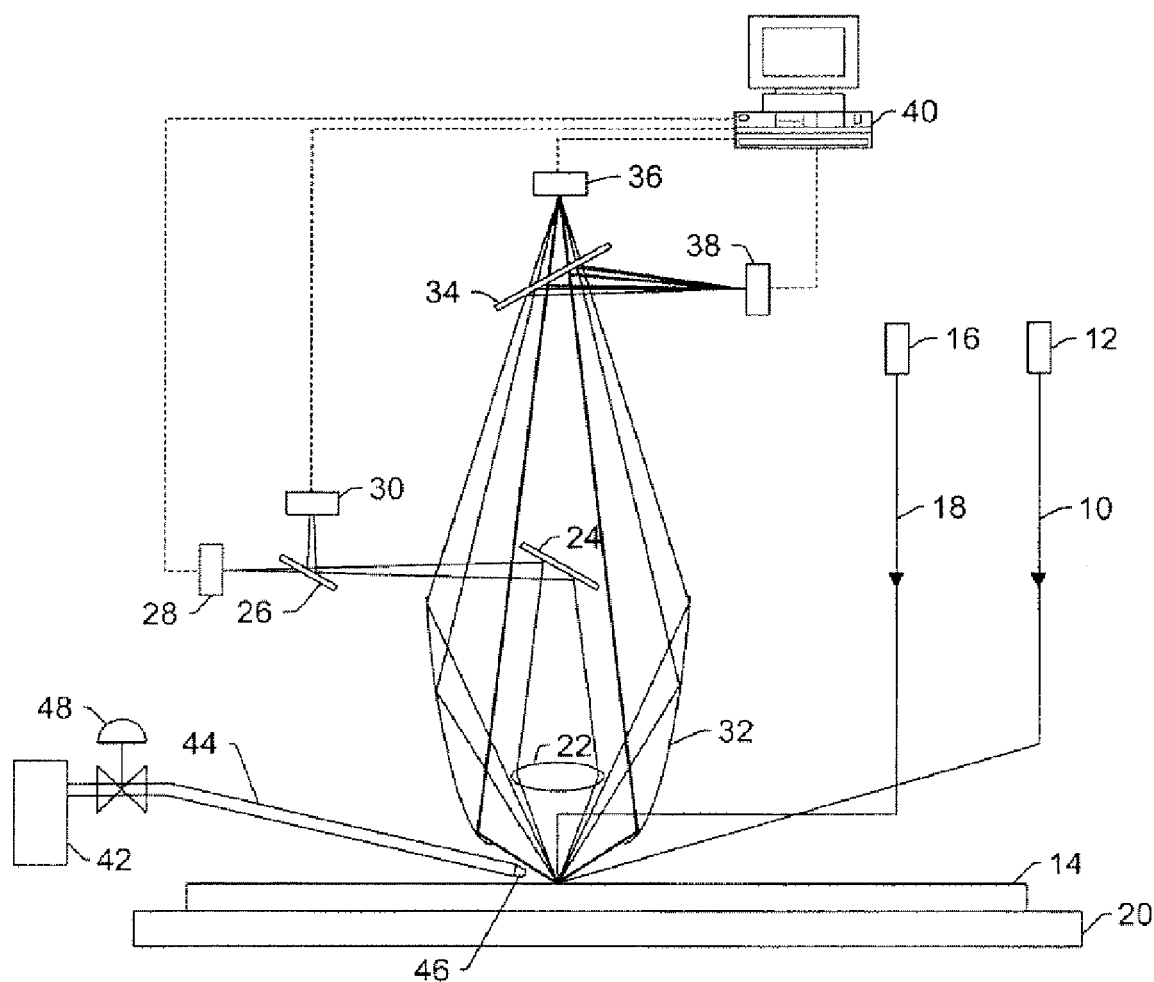
FIGS. 1-4 are schematic diagrams illustrating a cross-sectional view of various embodiments of a system that is configured to inspect a wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although embodiments are described herein for inspecting a wafer, it is to be understood that the embodiments described herein may configured and/or used for any other specimen, and in particular any specimen for which increased defect detection sensitivity is desirable.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment of a system that is configured to inspect a wafer is illustrated in FIG. 1. The system shown in FIG. 1 is configured for unpatterned wafer inspection and is based on the SP1-TBI system, which is commercially available from KLA-Tencor, San Jose, Calif. This inspection system is described in more detail in U.S. Pat. No. 6,538,730 to Vaez-Iravani et al., which is incorporated by reference as if fully set forth herein. The system shown in FIG. 1 may be further configured as described in this patent for patterned and unpatterned wafer inspection. For the sake of clarity, some of the components and details of the system have been omitted from FIG. 1 and the corresponding description presented herein. In addition, U.S. Pat. No. 6,538,730 is related to U.S. Pat. Nos. 6,201,601 to Vaez-Iaravani et al. and 6,271,916 to Marxer et al., which are also incorporated by reference as if fully set forth herein. The system shown in FIG. 1 may be further configured as described in these patents.

The system shown in FIG. 1 includes an inspection subsystem configured to direct light to a spot on the wafer and to generate output signals responsive to light scattered from the spot on the wafer. In one embodiment, the inspection subsystem is configured as an unpatterned wafer inspection subsystem. In another embodiment, the inspection subsystem is configured as a laser-based inspection subsystem. In an additional embodiment, the inspection subsystem is configured as a scanning-based inspection subsystem. In addition, the inspection subsystem may be configured as a laser- and scanning-based unpatterned wafer inspection subsystem.

The inspection subsystem may be configured to generate light 10. For instance, the inspection subsystem may include light source 12, which is configured to generate light 10.

The inspection subsystem is configured to direct light 10 to a spot (not shown) on wafer 14 at an oblique angle of incidence. In one embodiment, light 10 directed to the spot on the wafer includes ultraviolet (UV) light. The inspection subsystem may include a number of optical components (not shown) positioned in a path of light 10 such as folding mirror(s), beam splitter(s), polarizing component(s), filter(s), and lenses. The angle of incidence may vary depending on, for example, the characteristics of the light and the characteristics of the specimen. One suitable angle of incidence may be about 70° from normal to the upper surface of the wafer.

The inspection subsystem also includes light source 16. Light source 16 is configured to generate light 18, which is directed by the inspection subsystem to the spot on wafer 14 at a substantially normal angle of incidence. In one embodiment, light 18 directed to the spot on the wafer includes UV light. The inspection subsystem may include a number of optical components (not shown) positioned in the path of light 18. These optical components may include any of those described above.

Light sources 12 and 16 may include any suitable light sources known in the art such as lasers. In a different embodiment, the inspection subsystem may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The inspection subsystem may include any other suitable combination of a single light source and beam multiplier(s) known in the art. In any of the above embodiments, light 10 may have one or more characteristics such as wavelength and/or polarization that are different than the characteristics of light 18. Alternatively, light 10 may have substantially the same characteristics as light 18.

Wafer 14 is supported on stage 20, which may be rotated and translated such that light 10 and 18 illuminates an area or spot that moves on the wafer in a spiral path. Alternatively, light 10 and 18 may be scanned over the wafer in any manner known to those skilled in the art to trace the spiral path or another type of scan path across the wafer.

Illumination of the wafer will cause scattering of the light from the wafer. In addition, both oblique incidence light and normal incidence light may be scattered from the wafer. The inspection subsystem is configured to collect light scattered from the wafer and to generate output signals responsive to the scattered light. The output signals can be used to detect defects on the wafer as described further herein.

The inspection subsystem includes lens collector 22, mirror 24, beam splitter 26, and detectors 28 and 30, which form a "narrow" channel of the inspection subsystem. In other words, light scattered from the illuminated spot on the wafer along directions relatively close to normal to the surface of the wafer is collected and focused by lens collector 22. In this manner, lens collector 22 collects light scattered from the wafer at relatively "narrow" scattering angles. Lens collector 22 directs the collected light to mirror 24, which directs the light to beam splitter 26. Beam splitter 26 is configured to direct one portion of the light to detector 28 and the other portion of the light to detector 30. One detector may be used to detect light scattered at relatively narrow angles due to illumination by the normal incidence beam, and the other detector may be used to detect light scattered at relatively narrow angles due to illumination by the oblique incidence beam. Detectors 28 and 30 may include any suitable detectors known in the art (e.g., photomultiplier tubes (PMTs)). In addition, detectors 28 and 30 may be similarly or differently configured. The narrow channel portion of the inspection subsystem may include any other optical components (not shown) known in the art. For example, one or more polarizing components may be placed in the path of the collected light. In addition, a spatial filter may be included in the narrow channel portion of the inspection subsystem to prevent the specular reflection of the normal incidence beam from reaching detectors 28 and 30.

The inspection subsystem also includes ellipsoidal mirror 32, beam splitter 34, and detectors 36 and 38, which form a "wide channel" of the inspection subsystem. In other words, light scattered from the illuminated spot on the wafer along directions relatively far from normal to the surface of the wafer is collected and focused by ellipsoidal mirror 32. In this manner, ellipsoidal mirror 32 collects light scattered from the wafer at relatively "wide" scattering angles. Ellipsoidal mirror 32 directs the collected light to beam splitter 34. Beam splitter 34 is configured to direct one portion of the light to detector 36 and the other portion of the light to detector 38. One detector may be used to detect light scattered at relatively wide angles due to illumination by the normal incidence beam, and the other detector may be used to detect light scattered at relatively wide angles due to illumination by the oblique incidence beam. Detectors 36 and 38 may include any suitable detectors known in the art (e.g., PMTs). In addition, detectors 36 and 38 may be similarly or differently configured. The wide channel portion of the inspection subsystem may include any other optical components (not shown) known in the art. For example, one or more polarizing components may be placed in the path of the collected light.

Detectors 28, 30, 36, and 38 are configured to generate output signals responsive to the scattered light. Processor 40 is coupled to detectors 28, 30, 36, and 38 by transmission media as shown by the dotted lines in FIG. 1. The transmission media may include any suitable transmission media known in the art. In addition, one or more additional components (not shown) may be interposed between the detectors and the processor such as analog-to-digital converters. In this manner, output signals generated by the detectors can be sent to the processor. The processor is configured to detect defects on the wafer using the output signals. The processor may be configured to use any algorithm or method known in the art for detecting the defects using the output signals. In addition, the processor may include any suitable processing component known in the art.

Although the inspection subsystem embodiments are described above with respect to SP1 and SP2 based systems, which are commercially available from KLA-Tencor, it is to be understood that the system embodiments described herein can be implemented using any suitable surface inspection subsystem (e.g., multi-spot systems, acousto-optic deflector (AOD) scanning systems, streak-detector based systems, etc.).

The system shown in FIG. 1 also includes a gas flow subsystem configured to replace a gas located proximate to the spot on the wafer with a medium that scatters less of the light than the gas thereby increasing the sensitivity of the system. The gas located proximate to the spot on the wafer that is replaced by the medium may include the gas that is located in the collection space of the collection optics (e.g., lens collector 22 and ellipsoidal mirror 32) of the inspection subsystem since it is the light scattering that occurs due to the gas in the collection space that reduces the sensitivity of the system. The presence of the medium proximate to the spot on the wafer preferably reduces background Rayleigh scattering from the atmosphere that would otherwise be a limiting factor for the achievable sensitivity of the inspection subsystem if perfect mirror-smooth silicon wafer surfaces scattered 0 ppb of the incident light. In one embodiment, the increased sensitivity of the system is sufficient for detecting polystyrene latex (PSL) spheres having a diameter of about 25 nm on bare polished silicon wafers. Of course, such a system will also have sufficient sensitivity for detecting PSL spheres having a diameter of greater than about 25 nm.

In one embodiment, the gas flow subsystem includes gas source 42. Gas source 42 may have any suitable configuration known in the art such as a bottle, a tank, a house supply, etc. In addition, the configuration of gas source 42 may vary depending on the type of gas contained therein. The gas flow subsystem also includes conduit 44 that is coupled to gas source 42. Conduit 44 may have any suitable configuration (e.g., diameter, composition, etc.) known in the art and may be coupled to gas source 42 in any manner known in the art. In addition, the configuration of conduit 44 may vary depending on the type of gas that flows through the conduit and the flow characteristics of the gas in the conduit. As shown in FIG. 1, conduit 44 extends from gas source 42 to a position proximate to the spot on the wafer that is illuminated by the inspection subsystem. However, it is to be understood that the gas flow subsystem may actually include any number of conduits that in combination convey gas from gas source 42 to the position proximate to the illuminated spot on the wafer.

As further shown in FIG. 1, conduit 44 may include nozzle 46 coupled to the end of the conduit located proximate to the illuminated spot on the wafer. Nozzle 46 may include any appropriate nozzle known in the art and may be selected based on the gas that flows through the nozzle and other selected flow characteristics of the gas exiting nozzle 46 (e.g., flow rate, pressure, etc.). The gas flow subsystem may also include valve 48 coupled to conduit 44. Valve 48 may include any suitable valve known in the art having any suitable configuration known in the art. In addition, although the gas flow subsystem is shown in FIG. 1 as including one valve, it is to be understood that the gas flow subsystem may include any number of gas control devices that are configured to control the flow of the gas through conduit 44. The gas flow subsystem may also include any other appropriate gas flow devices known in the art.

As described above, the configuration of the gas flow subsystem may vary depending on the type of gas that is delivered proximate to the illuminated spot on the wafer by the gas flow subsystem. The configuration of the gas flow subsystem may also vary depending on the configuration of the inspection subsystem. For instance, as described above, the gas flow subsystem is configured to replace a gas located proximate to the spot on the wafer with a medium that scatters less of the light directed to the spot than the gas thereby increasing the sensitivity of the system. In this manner, the configuration of the gas flow subsystem may be selected based on the size of the illuminated spot on the wafer and the configuration of the collection optics (e.g., such that the entire volume of gas previously located proximate to the spot on the wafer in the collection space of the collection optics is replaced with the medium by the gas flow subsystem).

The gas flow subsystem may also be configured such that the medium flows across the illuminated spot on the wafer in a particular manner (e.g., laminar flow versus turbulent flow). Furthermore, as described above, the inspection subsystem may be configured such that the stage and therefore the wafer move during inspection such that the wafer can be scanned by the inspection subsystem. As such, the gas flow subsystem may be configured based on the movement of the wafer such that the medium can be located proximate to the illuminated spot on the wafer during an entire scan of the wafer thereby substantially preventing the gas previously located proximate to the illuminated spot on the wafer from being in the collection paths of the inspection subsystem proximate to the illuminated spot during inspection. For instance, the gas flow subsystem can be configured such that the aerodynamic effects of the spinning and linear scanning movement of the wafer in the laser surface inspection system that may reduce the effectiveness of the scattering "shield" can be mitigated. Furthermore, the gas flow subsystem may be configured such that the characteristics of the medium proximate to the illuminated spot on the wafer do not change substantially during inspection of the wafer. In this manner, the amount of light that is scattered by the medium during the entire inspection process may be substantially constant thereby increasing the repeatability of the inspection subsystem. The particular gas flow subsystem that is suitable for a particular inspection subsystem may be determined using mass transfer principles known to those skilled in the art, which will not be described further herein for the sake of clarity.

As described above, the gas flow subsystem is configured to replace a gas located proximate to the spot on the wafer with a medium that scatters less of the light than the gas thereby increasing the sensitivity of the system. The inspection subsystem may include one or more lasers. In this manner, in some embodiments, the gas flow subsystem is configured to suppress atmospheric laser Rayleigh light scattering interferences in light scattering based surface inspection systems by replacing normal air present proximate to the spot on the wafer with a laser beam propagation medium that has a lower Rayleigh scattering cross-section than normal air.

Preferably, the medium has a refractive index at the operating wavelength(s) of the inspection subsystem that is lower than the refractive index of dry air at the operating wavelength (s). For example, the inspection subsystem may operate at visible and UV wavelengths. Therefore, in one embodiment, the medium preferably has a refractive index at visible and UV wavelengths that is less than the refractive index of dry air at the visible and UV wavelengths. In one preferred embodiment, the replacement medium is a gas that has the lowest known Rayleigh cross-section for visible and UV wavelengths (e.g., wavelengths from about 700 nm to about 200 nm).

In one embodiment, the medium consists essentially of elemental helium (He). In a different embodiment, the medium consists essentially of neon (Ne). As used herein, the term "consists essentially of" refers to a medium that includes one of the gases described above possibly in combination with other gases present in amounts that do not materially affect the basic characteristics of the light scattering caused by the medium. For instance, a medium that consists essentially of elemental helium or neon may include negligible amounts of dry air that do not materially affect the basic characteristics of the light scattering caused by the medium.

The gas flow subsystem may be configured to replace the atmosphere in the input beam line of the inspection subsystem with high purity elemental helium since high purity helium intrinsically scatters nearly two orders less light than normal air. In particular, near standard atmospheric temperature and pressure (STP: 273 K, 760 torr), both air and helium behave very nearly like ideal gases. From Rayleigh scattering theory, it can be shown that a given volume of two ideal gases at the same temperature and pressure will have relative scattering cross-sections equal to a function of the respective refractive indices of the gases (see, for instance, R. B. Miles, W. R. Lempert, J. N. Forkey, "Laser Rayleigh Scattering," Meas. Sci. Technol., 12 (2001) R33-R51, which is incorporated by reference as if fully set forth herein), according to the following equation:

$$\frac{\sigma_1}{\sigma_2} = \left(\frac{n_1 - 1}{n_2 - 1}\right)^2$$

where $\sigma_1$ is the Rayleigh cross-section of gas 1, $\sigma_2$ is the Rayleigh cross-section of gas 2, $n_1$ is the refractive index of gas 1, and $n_2$ is the refractive index of gas 2. At a wavelength of 589.3 nm, dry air at STP has a refractive index $n_1=1.000292$ while helium under the same conditions has a refractive index $n_2=1.000035$ (see, for example, Indices of air and gases at STP per www.webelements.com). Thus, the equation shown above indicates that substituting helium for air in an atmospheric pressure laser beam line reduces the Rayleigh scattering intensity nearly 70 fold.

Table 1 includes gas-phase refractive indices, n, (refractive indices at a temperature of 273 K and a pressure of 760 mm Hg for the sodium yellow d-line at 589.3 nm) and Rayleigh cross-section of the various gases relative to dry air, $\sigma_{Dry\ air}/\sigma_{gas}$. Only one noble gas other than helium, neon, would provide a substantial (19 fold) reduction in background scattering as shown by the refractive index of neon in Table 1. Hydrogen, being a diatomic molecule and therefore a more efficient dipole scatterer than dry air, would produce a 5 fold decrease in scattering background although its substantially high reactivity makes it an unattractive candidate for the systems and methods described herein. As further shown in Table 1, Argon (Ar), on the other hand, could actually increase background scattering somewhat, as its refractive index is slightly greater than humidified air (humidified air is shown in Table 1 as $H_2O(g)$).

TABLE 1

| Gas | n | $\sigma_{Dry\ air}/\sigma_{gas}$ |
| --- | --- | --- |
| He | 1.000035 | 70 |
| Ne | 1.000067 | 19 |
| $H_2$ | 1.000132 | 4.9 |
| $H_2O$ (g) | 1.000256 | 1.3 |
| Ar | 1.000281 | 1.08 |
| Dry air | 1.000292 | 1 |
| Kr | 1.000427 | 0.5 |
| Xe | 1.000702 | 0.2 |

Accurate methods for calculating the indices of air and helium at wavelengths of illumination used by inspection subsystems such as that described above are known in the art and have been experimentally verified. (See, for example, J. Stone and A. Stejskal, "Using helium as a standard of refractive index: correcting errors in a gas refractometer," Metrologia, 41 (2004) 189-97; L. R. Pendrill, "Macroscopic and microscopic polarizabilities of helium gas," J. Phys. B. At. Mol. Opt. Phys., 29 (1996) 3581-86; and Y. M. Chan and A. Dalgarno, "The refractive index of helium," Proc. Phys. Soc., 85 (1965) 227-30, which are incorporated by reference as if fully set forth herein.)

The refractive index of helium at a wavelength of 355 nm (used by some inspection subsystems including that described above) was calculated based on the work by J. Stone and A. Stejskal referenced above using the values shown in Table 2.

TABLE 2

| | |
|---|---|
| Temperature (K) | 293.15 |
| Pressure (Pa (=N m$^{-2}$)) | 101325 |
| λ (nm) | 355 |
| Boltzmann constant (J K$^{-1}$) | 1.3806503E−23 |
| Avogadro's number (mol$^{-1}$) | 6.02214199E+23 |
| B(T) (cm$^3$ mol$^{-1}$) | 11.826 |
| Density $\rho_0$ (mol cm$^{-3}$) | 4.1571E−05 |
| $Z_0$ | 1.0005E+00 |
| Density ρ (mol cm$^{-3}$) | 4.1551E−05 |
| $(\Delta Z)^2$ | 6.749691E−29 |
| $A_R$ (cm$^3$ mol$^{-1}$) | 0.5269686 |
| $B_R$ (cm$^6$ mol$^{-2}$) | −0.0613 |
| $(\Delta z)^2$ | 1.679601E−32 |

In Table 2, B(T) is the virial coefficient for the compressibility expansion, Z is the compressibility factor, $A_R$ is proportional to the atomic or molecular polarizability α, and $B_R$ the refractivity virial coefficient. The $B_R$ value shown in Table 2 is valid for wavelengths near 633 nm. Using the values shown in Table 2, the refractive index of helium at 355 nm was calculated to be 1.000032844. In addition, the refractive index of helium at a wavelength of 355 nm was calculated based on the work by Y. M. Chan and A. Dalgarno referenced above to be 1.00003527.

The refractive index of humidified air was also calculated at a wavelength of 355 nm using the Engineering Metrology Toolbox that is available on the National Institute of Standards and Technology (NIST) website. In particular, the refractive index of air, $n_{Air}$, with 50% relative humidity and 450 ppm carbon dioxide ($CO_2$) was calculated to be 1.000280423 (using the Ciddor Equation). In addition, $n_{Air}$ with 50% relatively humidity was calculated to be 1.000280424 (using the Modified Edlén Equation).

Therefore, it is expected that the reduction factor at the actual 355 nm UV wavelength used by inspection subsystems such as the inspection subsystem described above will be comparable to the reduction factors described above for helium and neon. In particular, based on the values of the refractive indices of helium and air at a wavelength of 355 nm calculated above, the worst case for $\sigma_{Air}/\sigma_{He}$ was calculated to be 63.2 while the best case for $\sigma_{Air}/\sigma_{He}$ was calculated to be 72.9. As such, using helium as a medium in embodiments described herein should reduce background scattering by a factor of about 60 to about 70 at a wavelength of 355 nm.

Due to the high degree of precision with which the refractive index of helium may be calculated as a function of temperature and pressure, Stone et al. (J. Stone and A. Stejskal, "Using helium as a standard of refractive index: correcting errors in a gas refractometer," *Metrologia*, 41 (2004) 189-97, which is incorporated by reference as if fully set forth herein) proposed using helium to fill high-precision optical resonators thereby creating highly precise wavelength standards. Although Rayleigh scattering is one of the modes by which a laser pulse "rings down" in such a resonator, Stone et al. used helium, not for its lower Rayleigh scattering cross-section, but because this cross-section (as given by the index of refraction) can be calculated more accurately than for air.

Sun et al. (J. Sun, J. P. Longtin, "Effects of Gas Medium on Femtosecond Laser Beam Delivery," 21st International Congress on Applications of Lasers & Electro-Optics (ICALEO 2002), Scottsdale, Ariz., U.S.A., Oct. 14-17, 2002; J. Sun, J. P. Longtin, "Inert Gas Beam Delivery for Ultrafast Laser Micromachining at Ambient Pressure," *J. Appl. Phys.*, 89 (2001) 8219-24; J. Sun, J. P. Longtin, "Novel Beam Delivery Technique for Ultrafast Laser Processing," *Thermal Sci. & Eng.*, 7 (1999) 81-85, which are incorporated by reference as if fully set forth herein) propose helium as a laser propagation medium for femtosecond pulsed lasers used for fine resolution machining. The power density of a sub-picosecond laser pulse induces a non-linear optical effect in air since the index of refraction in effect becomes a function of laser intensity, which distorts both the temporal and spatial shape of the laser beam. Not surprisingly, the higher order optical non-linearity of a helium atmosphere is far less than air so pulse distortion and self-defocusing effects may be minimized using helium without resorting to a vacuum from the propagation medium.

Although the work by Stone et al. and Sun et al. realizes the benefits of using helium as a laser propagation medium to avoid the expense and difficulty of performing scientific measurements or machining operations in a vacuum, the problem solved is not a result of linear, Rayleigh light scattering, but of higher order non-linear effects to which continuous-wave lasers generally used in unpatterned wafer inspection are not subject. However, there appears to be no references in the scientific and technical literature explicitly citing helium or any other lower refractive index gas (relative to air) as an alternative beam propagation medium for the suppression of Rayleigh scattering interference.

As shown in FIG. 1, the gas flow subsystem is configured to replace the gas with the medium only at a location proximate to the spot on the wafer. For instance, a relatively small, gaseous "sheath" of the medium such as helium or neon can be directed at and about the beam spot on the wafer. Preferably, the helium displaces nitrogen, oxygen, and other trace gasses in the atmosphere having relatively large Rayleigh scattering cross-sections in the critical volume (i.e., the collection space) where Rayleigh scattering is "visible" to the detectors of the inspection subsystem thereby effecting a nearly two order of magnitude reduction in background scattering.

Such embodiments of the gas flow subsystem are advantageous for a number of reasons. For example, by directing a relatively small jet of the medium into the critical volume far less of the medium will be consumed than if the entire space within the inspection subsystem is replaced with the medium. In this manner, the gas source described above may be standard bottled helium or a house helium service line in semiconductor fabrication facilities so equipped, and recovery of the small amounts of helium used during scans would not be necessary. Therefore, replacing the gas with the medium only at the location proximate to the spot on the wafer reduces the operating cost of the system compared to the cost of a gas flow subsystem that is configured to replace the gas within the entire inspection subsystem with the medium. The system shown in FIG. 1 may be further configured as described herein.

The "helium jet" embodiments described above do not reduce or eliminate photodecomposition of trace organic vapors on the optics of powerful UV laser inspection subsystems. Such photodecomposition can take place on refractive and reflective optical components of the inspection subsystems. In one embodiment, the system includes a housing surrounding one or more optical components of the inspection subsystem. In one such embodiment, the gas flow subsystem is configured to purge the housing the medium and to maintain a positive pressure in the housing the medium such that photodecomposition of materials on the one or more optical components (e.g., one or more refractive and/or reflective optical components of the inspection subsystem) is reduced.

Figure 2:
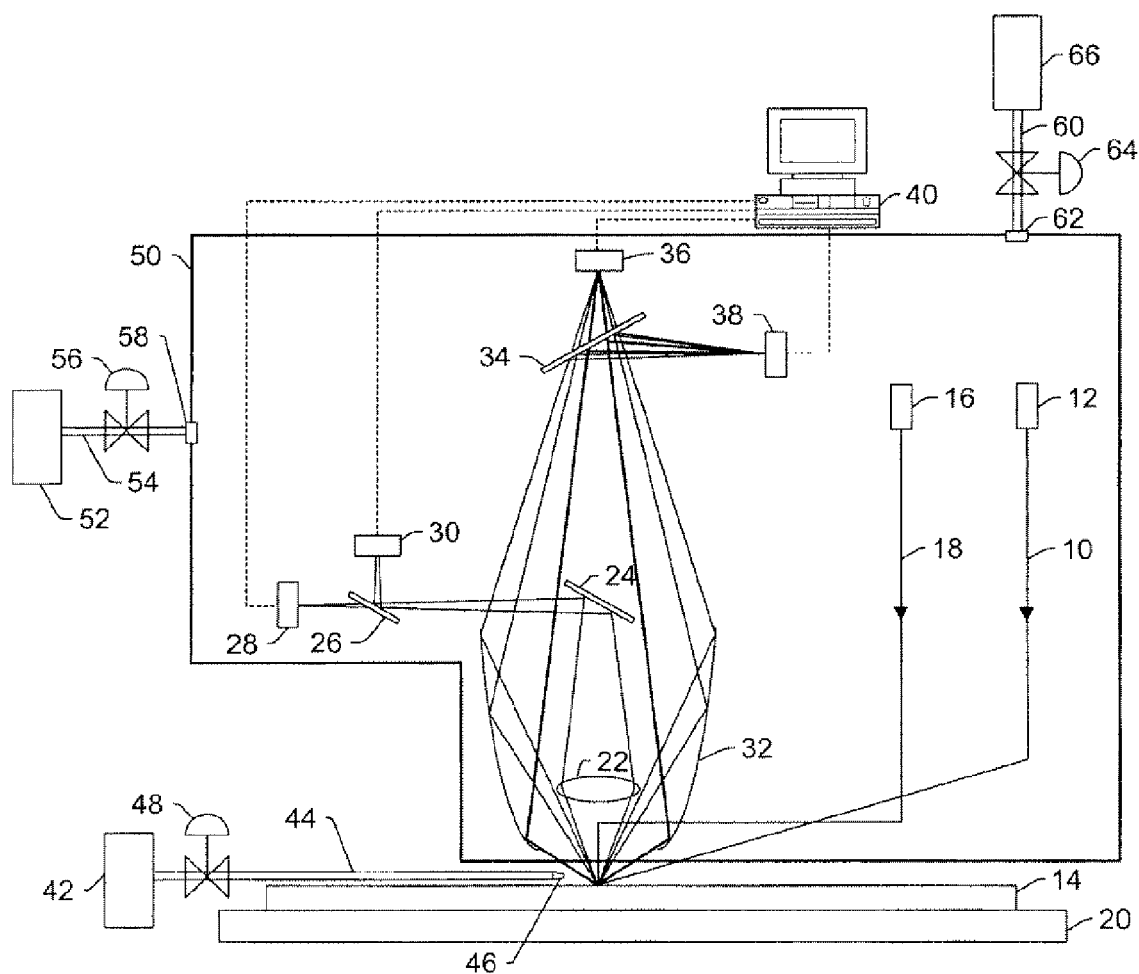

One such embodiment is shown in FIG. 2. In particular, the system shown in FIG. 2 includes housing 50 surrounding one or more optical components of the inspection subsystem. In particular, housing 50 surrounds light sources 12 and 16, lens collector 22, mirror 24, beam splitter 26, detectors 28 and 30, ellipsoidal mirror 32, beam splitter 34, and detectors 36 and 38. Therefore, housing 50 surrounds all of the optical components of the inspection subsystem. However, housing 50 may surround only a portion of the optical components of the inspection subsystem (e.g., the optical components configured for illumination of the spot on the wafer). Housing 50 may have any suitable configuration known in the art. In addition, housing 50 may include a "window" (not show) inserted into the body of the housing across the area of the housing that the light directed to the spot on the wafer and the light scattered from the spot on the wafer travel through. The window may be formed of any material that will not substantially alter the properties (e.g., intensity, wavelength, polarization, etc.) of the light directed to the spot on the wafer and the light scattered from the spot on the wafer.

The gas flow subsystem is coupled to housing 50 such that the gas flow subsystem can purge the housing the medium and to maintain a positive pressure in the housing the medium. For instance, the gas flow subsystem may include gas source 52 that is coupled to conduit 54. Gas source 52 and conduit 54 may be configured as described above. Valve 56 is coupled to conduit 54, and valve 56 may be configured as described above. Conduit 54 is coupled to housing 50 by coupling 58. Coupling 58 may include any suitable coupling known in the art that can be used to create a relatively gas tight seal between conduit 54 and housing 50. In this manner, the gas flow subsystem may be configured to transfer a medium from gas source 52 through valve 56 and conduit 54 into housing 50. The gas flow subsystem also includes conduit 60 coupled to housing 50 by coupling 62. Valve 64 is coupled to conduit 60. Conduit 60 is also coupled to collection vessel 66. Conduit 60, coupling 62, and valve 64 may be configured as described herein. Collection vessel 66 may include any suitable collection vessel known in the art. The gas flow subsystem may be configured to remove one or more gases from housing 50 through conduit 60 and into collection vessel 66. Therefore, to purge housing the medium, the gas flow subsystem may be configured to flow the gas medium into housing 50 from gas source 52 and to flow gas out of the housing into collection vessel 66 until approximately all of the gas has been removed from the housing and replaced with the medium. Then, a positive pressure may be created and maintained in housing 50 by closing valve 64 and transferring additional gas from gas source 52 into housing 50.

The medium that is used to purge the housing and to maintain a positive pressure in the housing may include any of the media described above. In addition, as shown in FIG. 2, the gas flow subsystem may also be configured to replace the gas with the medium at a location proximate to the spot on the wafer using gas source 42, conduit 44, nozzle 46, and valve 48. In this manner, one portion of the gas flow subsystem shown in FIG. 2 may be configured to purge the housing the medium and to maintain a positive pressure inside the housing the medium, and another portion of the gas flow subsystem is configured to replace the gas with the medium only at a location proximate to the spot on the wafer. The portion of the gas flow subsystem configured to purge the housing and to maintain a positive pressure in the housing may be further configured as described herein. Such embodiments of the gas flow subsystem may be useful when the housing is spaced from the wafer such that a relatively large volume of the gas is present in that volume until replaced by the medium as described above since the relatively large volume of the gas may substantially scatter the light.

In addition, if the housing has an opening (not shown) in the body of the housing such that the light is directed to the spot on the wafer through the opening and light scattered from the spot on the wafer travels through the opening, the positive pressure in the housing created using the medium may effectively "push" the medium out of the opening into the space between the lower surface of the housing and the upper surface of the wafer thereby effectively replacing any other gas that is present in that space. However, such a housing configuration may result in the consumption of a larger amount of helium than if the housing includes the window described above and may result in the need to recover the helium from the atmosphere external to the housing. Therefore, the housing may be effectively sealed from the external environment by sealing devices (not shown) that allow components of the system such as the transmission media from the detectors to the processor to pass through the housing while substantially preventing gas from leaking out of the housing. In addition, as described above, the housing may include a window that allows the light of the inspection subsystem to pass from the inspection subsystem to the wafer and vice versa. In such instances, the medium within the housing cannot be used to replace the gas located proximate to the spot on the wafer between the housing and the wafer. Therefore, the gas flow subsystem may use gas source 42, conduit 44, nozzle 46, and valve 48 as described above to replace this gas with the medium.

The medium that is used to purge the housing and to maintain the positive pressure in the housing may be the same as the medium that is used to replace the gas located proximate to the spot on the wafer. Alternatively, the medium that is used to purge the housing and to maintain the positive pressure in the housing may be different than the medium that is used to replace the gas located proximate to the spot on the wafer. In such instances, both media may include media that have a refractive index at the operating wavelength(s) of the inspection subsystem that is less than the refractive index of dry air at the operating wavelength(s) of the inspection subsystem.

The embodiments of the system shown in FIG. 2 have a number of advantages over currently available inspection systems. For example, if a relatively high power UV laser source is implemented in the inspection subsystem, the UV laser energy density at a plurality of optical surfaces in the input beam forming optics may approach a level at which decomposition of trace organic vapors in the air degrade the optics over time thereby leading to reliability degradation and substantially expensive maintenance costs involving precision optics handling and alignment in the field. However, the embodiment of the system shown in FIG. 2 is configured to replace the atmosphere in the input beam line with high purity helium, which intrinsically scatters nearly two orders less light than normal air, and at the same time provides a nearly contaminant free environment that extends the life of high energy density UV optical elements.

For some inspection systems, certain parts of the optical enclosure are deliberately left open so that vibrations from the rotating scan stage are not transmitted to the optics casting. Therefore, if a helium purge is performed within such an optical enclosure, the helium purge requires a relatively large volume of the medium and is more costly than other high purity gases such as nitrogen for purging and maintaining a clean atmosphere in and around the beam line optics. However, with judicious use of flexible or vibration absorbing sealing materials or re-engineering a vibration isolation system between the optics casting and the mechanical subsystem of the inspection subsystem, it would be feasible to purge the optical enclosure with helium, then close one or more purging outlet valves, and bring the enclosure up to a slight positive pressure relative to the surroundings, which may be controlled by a gas pressure regulator. The optical enclosure then requires only relatively small amounts of make-up gas as helium leaks out of the residual gaps in the optical enclosure seals. The purging operations described herein may be performed at the time the laser is first powered up and after each subsequent maintenance event requiring opening of the optical enclosure. The system shown in FIG. 2 may be further configured as described herein.

Figure 3:
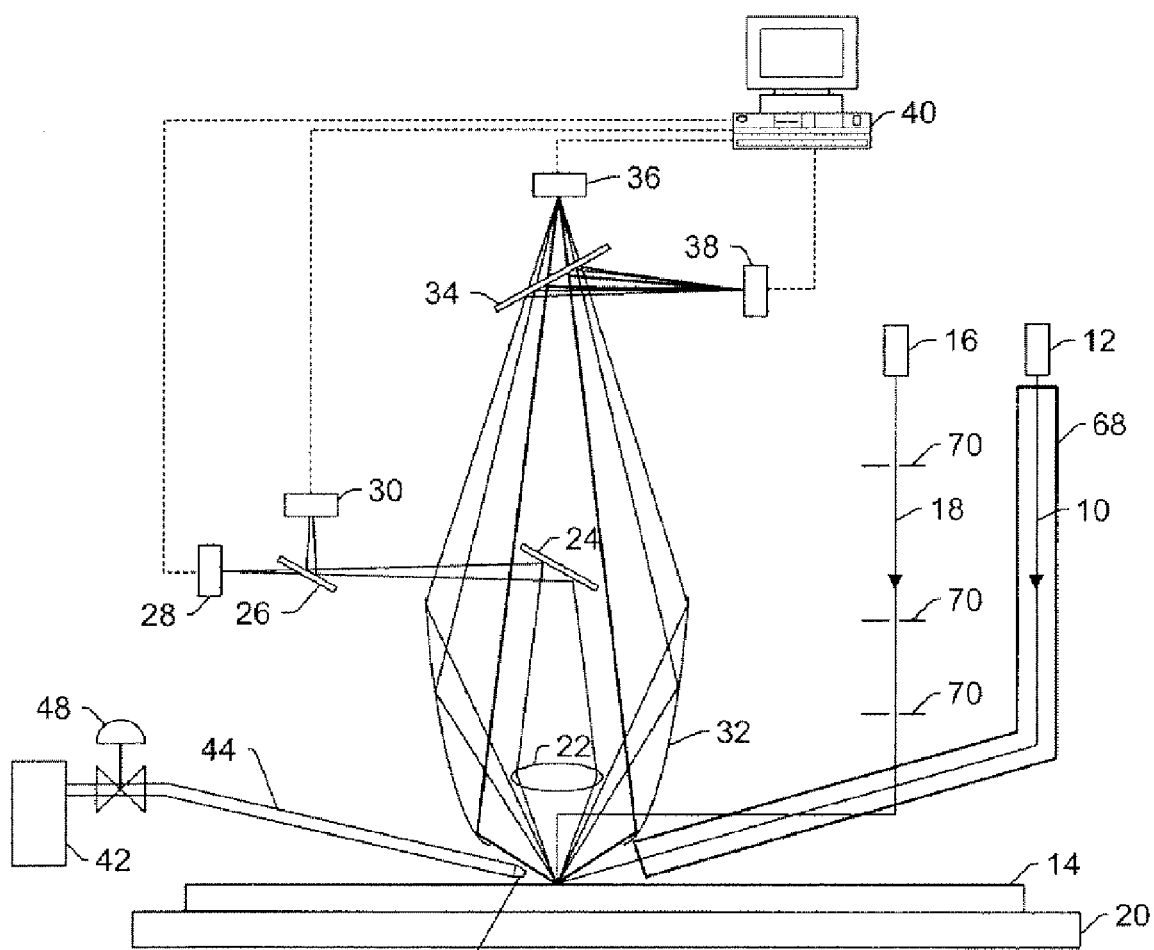

In some embodiments, the inspection subsystem includes one or more optical components configured to block light scattered along an illumination path of the inspection subsystem such that the output signals are not responsive to the light scattered along the illumination path. One such embodiment is illustrated in FIG. 3. As shown in FIG. 3, the inspection subsystem includes optical component 68 configured to block light scattered along the illumination path of the inspection subsystem along which light 10 travels such that the output signals generated by detectors 28, 30, 36, and 38 are not responsive to the light scattered along this illumination path. In one embodiment, optical component 68 may include baffles. The baffles may include any suitable baffles or field stops known in the art that can be used to block stray photons.

In addition, the inspection subsystem includes optical components 70 that are configured to block light scattered along the illumination path of the inspection subsystem along which light 18 travels such that the output signals generated by detectors 28, 30, 36, and 38 are not responsive to the light scattered along this illumination path. In one embodiment, optical components 70 include apertures. The apertures may include any appropriate apertures known in the art. Although three apertures are shown in FIG. 3 positioned along the illumination path of light 18, it is to be understood that the system may include any suitable number of such optical components.

Therefore, the optical components configured to block scattered light along different illumination paths of the inspection subsystem may be different. Alternatively, the optical components configured to block scattered light along different illumination paths of the inspection subsystem may be substantially the same. In addition, one or more of the optical components may be configured to block scattered light along only one (or some) of the illumination paths of the inspection subsystem. Furthermore, more than one type of the optical components (e.g., baffles and apertures) may be configured to block scattered light along one (or some) of the illumination paths of the inspection subsystem.

In some inspection subsystems, atmospheric Rayleigh scattering occurs through the beam line from the laser head through the beam forming optics and down to the spot of incidence/reflection on the wafer. However, as described above, the beam line may be engineered with appropriate baffling and/or apertures to block stray, scattered light from reaching the scattered light detection optics, which are specifically designed to be "blind" to light except that coming from the incident spot on the wafer. Therefore, only the relatively small volume of the atmosphere in the region just above the beam spot on the wafer may be replaced with the medium by the gas flow subsystem to effectively reduce the scattering of the light by the atmosphere thereby increasing the sensitivity of the system.

Accordingly, although the entire atmosphere inside an unpatterned wafer inspection system may be conceivably replaced with helium or another medium described herein, one need not go to such lengths to realize the benefits of the systems and methods described herein. Indeed, most wafer inspection systems pass relatively large volumes of ultra low penetration air (ULPA)-filtered air through the chamber in which a wafer is inspected so that trace particulate matter created by the scanning mechanics does not deposit on the wafer. It would be relatively expensive to run such a high volume of helium through the 10-12 unpatterned wafer systems in a typical 300 mm integrated circuit (IC) fabrication facility without the provision of a recovery and purification system for the medium. In addition, such a system would require a new investment of capital in a fabrication facility that could be put to better uses.

Therefore, the system shown in FIG. 3 is advantageous in that it mitigates the expense and complexity of purging relatively large volumes of normal atmosphere with helium by using illumination and collection optics that limit the interfering Rayleigh scattering to a relatively small volume in the general region of the illuminated spot on the wafer and arranging an apparatus to direct a relatively low volume of a helium gas stream into the small volume thereby replacing the atmosphere in the volume with a relatively low Rayleigh scattering "shield." The system shown in FIG. 3 may be further configured as described herein.

However, a system that is configured to replace the entire atmosphere inside the unpatterned wafer inspection system with helium or another medium described herein may be configured to recirculate flow of the medium from the ULPA filters into the housing and back to the ULPA filtration system. In this manner, the medium consumption per wafer would be significantly reduced compared to the open flow version described above. In such embodiments, a transfer chamber (not shown) may be included in the system. The wafer may be moved from the transfer chamber into the housing to reduce disturbances to the atmosphere in the housing. Such a system may also include a heat exchanger since there may no longer be a fresh air supply to the system.

Figure 4:
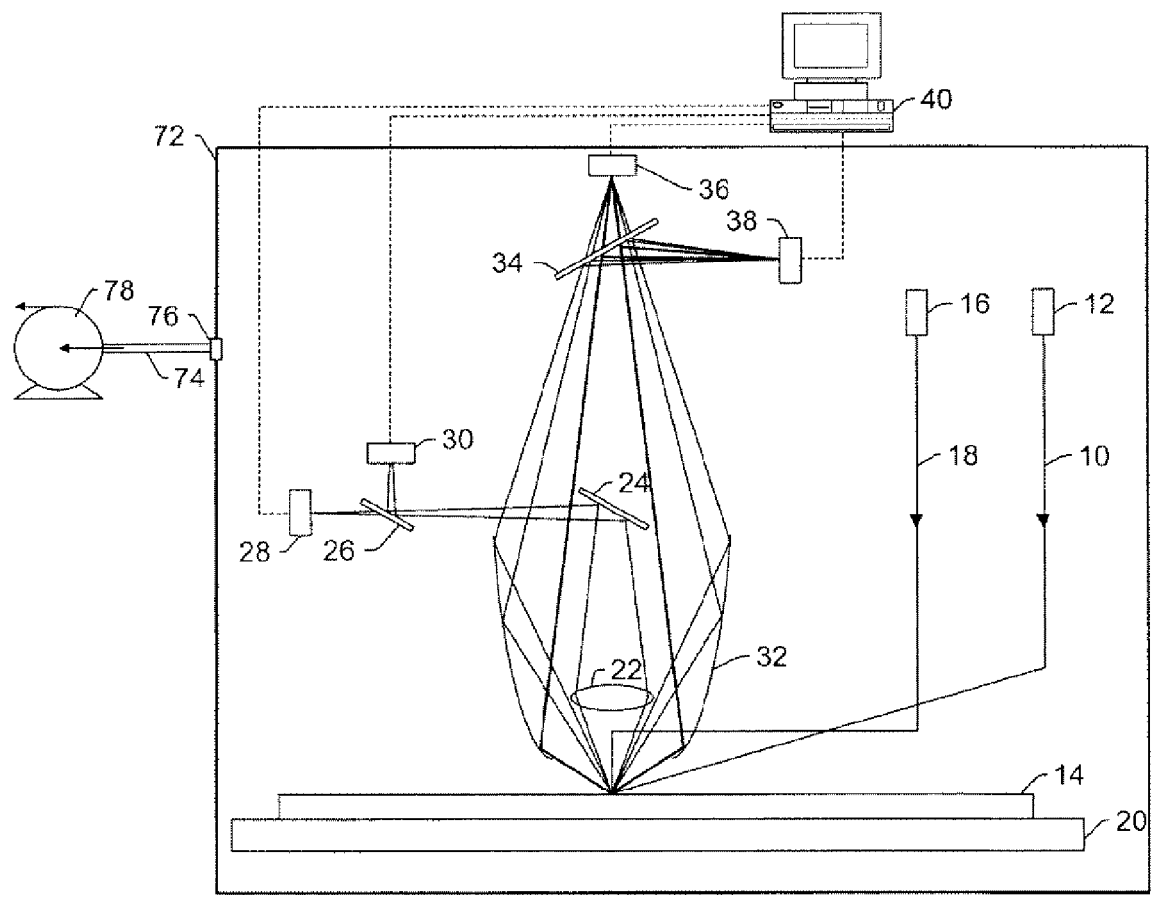

In another embodiment, the medium is a vacuum. One such embodiment of a system is shown in FIG. 4. As shown in FIG. 4, the system includes vacuum chamber 72 that surrounds the inspection subsystem including stage 20 and wafer 14 disposed thereon. Vacuum chamber 72 may have any suitable configuration known in the art. The gas flow subsystem includes conduit 74 coupled to vacuum chamber 72 via coupling 76. Conduit 74 and coupling 76 may have any suitable configuration known in the art. The gas flow subsystem also includes vacuum pump 78. Vacuum pump 78 may have any suitable configuration known in the art. Vacuum pump 78 is configured to create a vacuum in vacuum chamber 72 by removing gases from vacuum chamber 72 through conduit 74. In this manner, atmospheric scattering may be decreased in the system shown in FIG. 4 by removing the atmosphere (by evacuating air) in the scanning chamber with a vacuum pump. While feasible, this method for increasing the sensitivity of wafer inspection would add considerable cost and complexity to the inspection system, lower overall reliability, and increase maintenance costs compared to other system embodiments described herein. The system shown in FIG. 4 may be further configured as described herein.

Another embodiment relates to a gas flow subsystem configured to be coupled to an inspection system. The gas flow subsystem is also configured to replace a gas located proximate to a spot on a wafer illuminated by the inspection system during inspection with a medium that scatters less of the light than the gas thereby increasing the sensitivity of the inspection system. The gas flow subsystem may be further configured as described herein.

An additional embodiment relates to a method for inspecting a wafer. The method includes inspecting the wafer by directing light to a spot on the wafer and generating output signals responsive to light scattered from the spot on the wafer. The method also includes replacing a gas located proximate to the spot on the wafer during inspecting with a medium that scatters less of the light than the gas thereby increasing the sensitivity of the inspecting. In addition, the method includes detecting defects on the wafer using the output signals.

In one embodiment, the medium has a refractive index at visible and UV wavelengths that is less than the refractive index of dry air at the visible and UV wavelengths. In another embodiment, the medium consists essentially of elemental helium. In a different embodiment, the medium consists essentially of neon.

In one embodiment, replacing the gas includes replacing the gas with the medium only at a location proximate to the spot on the wafer. In another embodiment, the method includes purging a housing surrounding one or more optical components used for inspecting the wafer with the medium and maintaining a positive pressure in the housing the medium such that photodecomposition of materials on the one or more optical components is reduced. In some embodiments, the method includes blocking light scattered along an illumination path along which the light is directed to the wafer such that the output signals are not responsive to the light scattered along the illumination path. In a further embodiment, the medium includes a vacuum.

In some embodiments, the light directed to the spot on the wafer includes light generated by a laser. In another embodiment, the light directed to the spot on the wafer includes UV light. In an additional embodiment, inspecting the wafer includes scanning the spot across the wafer. In some embodiments, the increased sensitivity of inspecting the wafer is sufficient for detecting PSL spheres having a diameter of about 25 nm on bare polished silicon wafers.

Each of the steps of each of the embodiments of the method described above may be performed as described further herein. Each of the embodiments of the method described above may also include any other step(s) described herein. In addition, each of the embodiments of the method described above may be performed by one or more of the system embodiments described herein. Furthermore, each of the embodiments of the method described above has all of the advantages of the system embodiments described herein that can be used to perform the method embodiments.

The following example is not to be construed as a limiting embodiment of the invention and are included herein for example purposes only.

Example: Background Atmospheric Scattering with Normal Air and Helium Atmospheres The background atmospheric scattering of normal air and helium atmospheres was measured using an SP2 tool that included a 350 mW laser operating at a wavelength of 355 nm. The normal air atmosphere in the SP2 tool was replaced with a helium atmosphere by "flooding" the collector of the SP2 tool with high purity helium (>98% purity). The helium was provided to the system using a helium tank and a 400 mm long tube about 50 mm in diameter attached to the bottom of the wide collector (i.e., ellipsoidal mirror 32 described above). The helium was inserted about half way into the tube with an estimated flow rate on the order of 1 L/s. The helium flowed up into the collector thereby replacing some or most of the air in the collector. Openings in the middle section of the collector allowed the helium flow to "push" any residual air out of the collector. The scattering in the two different atmospheres was measured. In addition, the scattering of the normal incidence light and the oblique incidence light was measured using the wide collector. The detector used to measure the scattered light was a PMT set to a fixed gain of 5000 ADC counts/ppm. Table 3 includes results from these measurements.

TABLE 3

|  | Normal ST ADC | Scatter ppb | Oblique HT ADC | Scatter ppb |
| --- | --- | --- | --- | --- |
| Baseline | 127 | 25.4 | 98 | 19.6 |
| He-average | 46 | 9.2 | 26 | 5.2 |
| He-lowest | 44 | 8.8 | 20 | 4 |

In Table 3, "ST" refers to measurements performed with a spot size of about 10 µm×about 150 µm. "HT" refers to measurements performed with a spot size of about 10 µm×about 340 µm. "Baseline" indicates light scattering measurements performed in a normal air atmosphere. "He-average" indicates the average of the light scattering measurements performed in a helium atmosphere. Therefore, these measurements indicate the typical reproducible value obtained. "He-lowest" indicates the lowest value of the light scattering in a helium atmosphere that was measured more than once. The differences between the two measurement values obtained while the helium atmosphere was present in the tool may be a result of noise in the measurement or fluctuation in the purity of the helium. Error margins for the readings are on the order of 1 ppb for the individual readings and on the order of 10% for the gain calibration. The signal intensity measured in the experiment settled around its lowest values after about 5 seconds to about 10 seconds of helium purge was performed and fully recovered about 30 seconds to about 60 seconds after the helium flow was stopped.

As shown by the measurements in Table 3, by replacing normal atmospheric air with helium in the SP2 tool, the background scatter was reduced by about 4 to about 5 fold, which is less than the 70 fold theoretical values described above. Although the measurements shown in Table 3 indicate a smaller reduction in light scattering due to replacing the normal air atmosphere with a helium atmosphere than predicted theoretically, the lower light scattering reduction shown by the measurements in Table 3 may have been caused by some fraction of air left in the collector (an imperfect helium purge) plus some residual scatter from other sources in the system.

In the experiments described above, wafers were not scanned while the helium atmosphere was present in the tool. Therefore, although the results described above do not necessarily constitute a reduction to practice, the results do indicate that the systems and methods described herein can replace a gas located proximate to the spot on the wafer with a medium such as helium that scatters less of the light than the gas thereby increasing the sensitivity of the system.

Further modifications and alternative embodiments of various aspects of the invention may be apparent to those skilled in the art in view of this description. For example, systems and methods for inspecting a wafer with increased sensitivity are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
an inspection subsystem configured to direct light to a spot on the wafer and to generate output signals responsive to light scattered from the spot on the wafer, wherein the light directed to the spot on the wafer comprises ultraviolet light;
a gas flow subsystem configured to replace a gas located proximate to the spot on the wafer with a medium that scatters less of the light than the gas thereby increasing the sensitivity of the system, wherein the gas flow subsystem is further configured to replace the gas with the medium only at a location proximate to the spot on the wafer; and
a processor configured to detect defects on the wafer using the output signals.

2. The system of claim 1, wherein the medium has a refractive index at visible and ultraviolet wavelengths that is less than the refractive index of dry air at the visible and ultraviolet wavelengths.

3. The system of claim 1, wherein the medium consists essentially of elemental helium.

4. The system of claim 1, wherein the medium consists essentially of neon.

5. The system of claim 1, wherein the inspection subsystem comprises one or more optical components configured to block light scattered along an illumination path of the inspection subsystem such that the output signals are not responsive to the light scattered along the illumination path.

6. The system of claim 1, wherein the inspection subsystem is further configured as an unpatterned wafer inspection subsystem.

7. The system of claim 1, wherein the inspection subsystem is further configured as a laser-based inspection subsystem.

8. The system of claim 1, wherein the inspection subsystem is further configured as a scanning-based inspection subsystem.

9. The system of claim 1, wherein the increased sensitivity of the system is sufficient for detecting polystyrene latex spheres having a diameter of about 25 nm on bare polished silicon wafers.

10. A gas flow subsystem configured to be coupled to an inspection system, wherein the gas flow subsystem is further configured to replace a gas located proximate to a spot on a wafer illuminated by the inspection system during inspection with a medium that scatters less of the light than the gas thereby increasing the sensitivity of the inspection system, and wherein the gas flow subsystem is further configured to replace the gas with the medium only at a location proximate to the spot on the wafer.

11. A method for inspecting a wafer, comprising:
inspecting the wafer by directing light to a spot on the wafer and generating output signals responsive to light scattered from the spot on the wafer, wherein the light directed to the spot on the wafer comprises ultraviolet light;
replacing a gas located proximate to the spot on the wafer during said inspecting with a medium that scatters less of the light than the gas thereby increasing the sensitivity of said inspecting, wherein said replacing comprises replacing the gas with the medium only at a location proximate to the spot on the wafer; and
detecting defects on the wafer using the output signals.

12. The method of claim 11, wherein the medium has a refractive index at visible and ultraviolet wavelengths that is less than the refractive index of dry air at the visible and ultraviolet wavelengths.

13. The method of claim 11, wherein the medium consists essentially of elemental helium.

14. The method of claim 11, wherein the medium consists essentially of neon.

15. The method of claim 11, further comprising purging a housing surrounding only one or more optical components used for directing the light to the spot on the wafer with the medium and maintaining a positive pressure in the housing using the medium such that photodecomposition of materials on the one or more optical components is reduced.

16. The method of claim 11, further comprising blocking light scattered along an illumination path along which the light is directed to the wafer such that the output signals are not responsive to the light scattered along the illumination path.

17. The method of claim 11, wherein the light directed to the spot on the wafer further comprises light generated by a laser.

18. The method of claim 11, wherein said inspecting further comprises scanning the spot across the wafer.

19. The method of claim 11, wherein the increased sensitivity of said inspecting is sufficient for detecting polystyrene latex spheres having a diameter of about 25 nm on bare polished silicon wafers.

20. A system configured to inspect a wafer, comprising:
an inspection subsystem configured to direct light to a spot on the wafer and to generate output signals responsive to light scattered from the spot on the wafer;
a housing surrounding only one or more optical components of the inspection subsystem configured to direct the light to the spot on the wafer;
a gas flow subsystem configured to replace a gas located proximate to the spot on the wafer with a medium that scatters less of the light than the gas thereby increasing the sensitivity of the system, wherein the gas flow subsystem is further configured to purge the housing using the medium and to maintain a positive pressure in the housing using the medium such that photodecomposition of materials on the one or more optical components is reduced; and
a processor configured to detect defects on the wafer using the output signals.

* * * * *